United States Patent
Inoue et al.

(10) Patent No.: US 8,430,095 B2
(45) Date of Patent: Apr. 30, 2013

(54) BITE BLOCK

(75) Inventors: Masayuki Inoue, Tokyo (JP); Isao Matsubara, Tokyo (JP); Fumihiko Takatori, Tokyo (JP); Shinji Yamamori, Tokyo (JP)

(73) Assignee: Nihon Kohden Corporation, Tokyo (JP)

( * ) Notice: Subject to any disclaimer, the term of this patent is extended or adjusted under 35 U.S.C. 154(b) by 537 days.

(21) Appl. No.: 12/635,514

(22) Filed: Dec. 10, 2009

(65) Prior Publication Data

US 2010/0317987 A1  Dec. 16, 2010

(30) Foreign Application Priority Data

Dec. 11, 2008 (JP) ................... 2008-315637

(51) Int. Cl.
A61M 16/00 (2006.01)

(52) U.S. Cl.
USPC .......................... 128/200.26; 138/39; 138/114

(58) Field of Classification Search ............ 128/200.24, 128/200.26, 861, 859, 912, 201.18, 207.17, 128/207.14; 73/23.3; 600/543; 285/179, 285/179.1, 179.2; 138/39, 114
See application file for complete search history.

(56) References Cited

U.S. PATENT DOCUMENTS

| | | | | |
|---|---|---|---|---|
| 5,273,032 A * | 12/1993 | Borody | .................... | 128/207.14 |
| 5,513,634 A * | 5/1996 | Jackson | .................... | 128/207.18 |
| 5,537,994 A * | 7/1996 | Thornton | ................. | 128/204.18 |
| 5,752,510 A * | 5/1998 | Goldstein | ................ | 128/207.18 |
| 5,846,182 A * | 12/1998 | Wolcott | ......................... | 600/114 |
| 2002/0151871 A1 | 10/2002 | Gaiser et al. | | |
| 2005/0217678 A1 | 10/2005 | McCormick et al. | | |
| 2006/0278238 A1* | 12/2006 | Borody | ......................... | 128/848 |
| 2007/0006878 A1* | 1/2007 | Mackey et al. | .......... | 128/200.26 |
| 2007/0068535 A1 | 3/2007 | Colman et al. | | |
| 2008/0110456 A1* | 5/2008 | Flynn et al. | .............. | 128/200.26 |
| 2008/0295849 A1* | 12/2008 | Reynolds et al. | ............. | 128/859 |

FOREIGN PATENT DOCUMENTS

| | | |
|---|---|---|
| CA | 1 005 721 A1 | 2/1977 |
| GB | 2 401 795 A | 11/2004 |
| JP | A-2007-500566 A | 1/2007 |
| WO | WO 2005/016142 A | 2/2005 |

OTHER PUBLICATIONS

Extended European Search Report, Mar. 23, 2010.
Communication pursuant to Article 94(3) EPC issued by the European Patent Office, May 25, 2011.

* cited by examiner

*Primary Examiner* — Justine Yu
*Assistant Examiner* — Michael Tsai
(74) *Attorney, Agent, or Firm* — Kenealy Vaidya LLP

(57) ABSTRACT

A bite block includes: a first wall defining a hole into which a conduit pipe is to be inserted; a second wall surrounding the first wall to define a flow path with the first wall; and a sample port communicating with the flow path.

10 Claims, 6 Drawing Sheets

BITE BLOCK

BACKGROUND OF THE INVENTION

The present invention relates to a bite block which is to be used in an examination by an endoscope, a rigid scope, or the like.

A related-art bite block which is to be used in an examination by an endoscope or the like, is known in which a gas sampling hole is formed in a space into which a conduit pipe is to be inserted, and prongs are coupled to the hole, thereby allowing respiration through the mouth to be measured (see JP-A-2007-500566). Furthermore, also a related-art bite block which has a similar configuration as described above, and which supplies oxygen to the oral cavity is known (see WO2005/016142).

In both the configurations, however, the hole is obstructed by secretion such as saliva during an examination, and there are problems in that the gas measurement cannot be adequately performed, and that the possibility of interrupting the oxygen supply is high. Moreover, a delay in response occurs in sampling, and a situation where a gas in the atmosphere is sucked occurs, thereby causing another problem in that the measured value is inaccurate.

SUMMARY

It is therefore an object of the invention to provide a bite block in which the measurement is prevented from being disturbed by secretion such as saliva, and the problem in that the measured value is inaccurate can be solved.

In order to achieve the object, according to the invention, there is provided a bite block comprising:

a first wall defining a hole into which a conduit pipe is to be inserted;

a second wall surrounding the first wall to define a flow path with the first wall; and a sample port communicating with the flow path.

The bite block may further include an attaching portion to which a respiration information collecting adaptor is to be attached.

The flow path may include a slope connected from the sample port to peripheral edges of the first and second walls.

The bite block may further include an adjustor provided at the sample port and coupled to a respiration information collecting adaptor, the adjustor configured to adjust an attitude of the respiration information collecting adaptor and a distance between the sample port and the respiration information collecting adaptor.

The sample port may include a divider partitioning an interior into a first chamber communicating with the flow path and a second chamber communicating with an outside.

The bite block may further include: an attaching portion; and a respiration information collecting adaptor attached to the attaching portion and configured to collect respiration information.

The respiration information collecting adaptor may include a holder holding a prong which supplies oxygen. When the bite block is attached to a subject, a tip end of the prong may be positioned near a nasal cavity or oral cavity of the subject.

The first wall may have a cylindrical shape. The conduit pipe may be connected to an endoscope or a rigid scope. The second wall may be to be directly opposed to an interior of an oral cavity of a subject. The flow path may be defined by a space between the first wall and the second wall. A gas in the oral cavity may be directed to the sample port through the flow path.

An end of the first wall to be opposed to an oral cavity of a subject may be in plane with an end of the second wall to be opposed to the oral cavity of the subject.

The hole defined by the first wall may be to be communicated with an outside and an oral cavity of a subject. The flow path defined by the first wall and the second wall may be to be communicated with the sample port and the oral cavity of the subject. The hole and the flow path may be separated with each other.

DETAILED DESCRIPTION OF EMBODIMENTS

Figure 1:
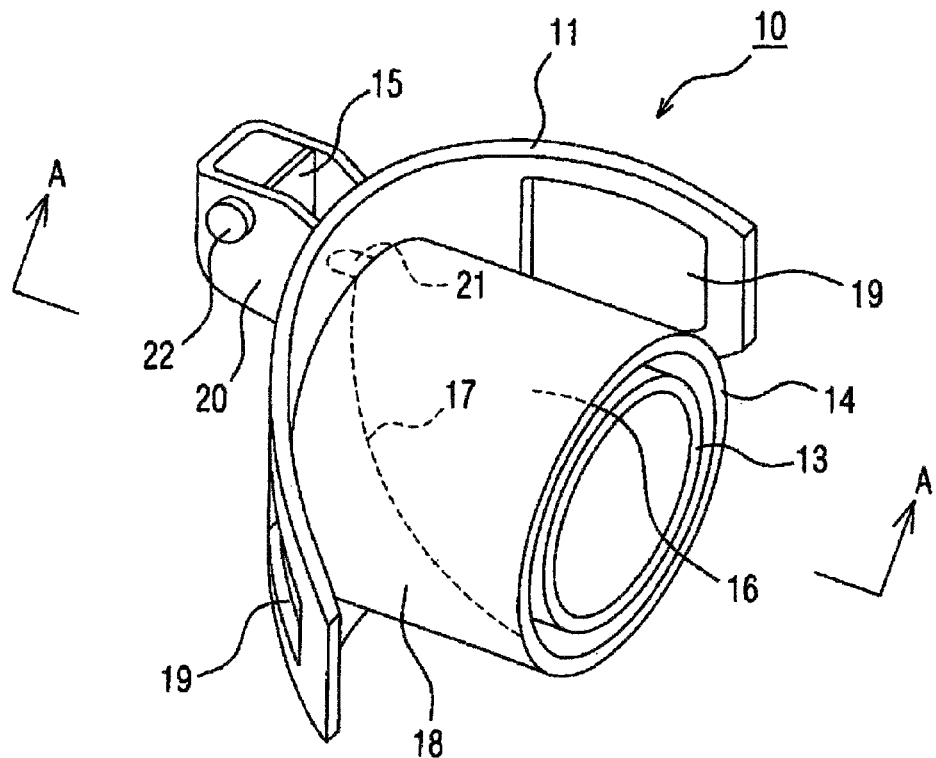
FIG. 1 is a perspective view of a bite block of an embodiment of the present invention.
Figure 2:
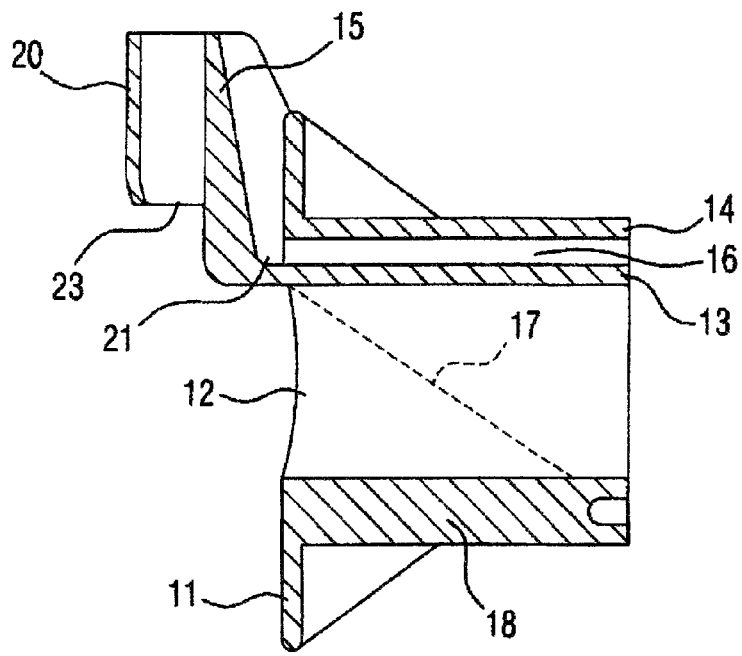
FIG. 2 is a sectional view taken along A-A in FIG. 1.

Hereinafter, an embodiment of the bite block of the invention will be described with reference to the accompanying drawings. In the figures, the identical components are denoted by the same reference numerals, and duplicated description will be omitted. FIG. 1 is a perspective view of the bite block of the embodiment, and FIG. 2 is a sectional view. The bite block 10 includes a plate portion 11 which is curved so as to butt against an opening lip portion of the subject, and which has a shape obtained by cutting off front and rear portions of, for example, an elliptical or boat-like shape. A hole 12 into which a conduit pipe of an endoscope is to be inserted is formed in a middle portion of the plate portion 11.

A cylindrical first wall 13 having a predetermined length stands from a position surrounding the hole 12 toward the rear face side of the plate portion 11 (in a use state, the inside of the oral cavity). A second wall 14 which surrounds the first wall, and which is to be directly opposed to the interior of the oral cavity is disposed on the same rear face of the plate portion 11. Namely, the outer peripheral edge of the second wall 14 is a portion which is to be contacted with the lips and the teeth.

A sample port 20 to which a respiration information collecting adaptor is to be attached, and which is used for taking in a gas in the oral cavity is disposed at the uppermost position of the surface of the plate portion 11. The sample port 20 has a shape of a cube like container, and one side wall of the port is configured as the plate portion 11. A space exists between the first wall 13 and the second wall 14. The space constitutes a gas flow path 16 which communicates with the sample port 20. In the one side wall which is the plate portion 11, a connection port 21 is disposed in the vicinity of the bottom face of the sample port 20. The sample port 20 and the gas flow path 16 communicate with each other through the connection port 21. The interior of the sample port 20 is partitioned by a divider 15 which is continuous to the first wall 13.

A hole 23 is formed in a bottom portion in the side where the connection port 21 is not disposed.

Bosses 22 are disposed approximately at the positions of the upper ends of the both side faces of the sample port 20, respectively. The bosses constitutes an adjusting mechanism which is coupling means that cooperates with notched holes of the respiration information collecting adaptor which will be described later, to be coupled to the respiration information collecting adaptor. The adjusting mechanism adjusts the attitude of the respiration information collecting adaptor, and the distance from the sample port 20 to the respiration information collecting adaptor.

The gas flow path 16 includes a slope 17 which is directed from the sample port 20 toward the peripheral edges of the first wall 13 and the second wall 14. In the slope 17, the connection port 21 in the sample port 20 is set as a starting point of the slope. The slope is gradually advanced in the space between the first and second walls 13, 14 toward the open ends of the first and second walls 13, 14, and finally connected to the most distal point as seen from the starting point in the open end of the bicylindrical structure formed by the first and second walls 13, 14. The slope is configured to be bilaterally symmetrical as seen from the starting point. A resin 18 which has the same composition as the bite block 10 is embedded in the inside with respect to the slope 17. The slope 17 is configured as described above. In a state where the bite block 10 is attached to the oral cavity, therefore, it is expected that the connection port 21 of the sample port 20 is the uppermost portion, and the most distal point in the open end of the bicylindrical structure formed by the first and second walls 13, 14 is the lowermost portion. Consequently, the slope functions so that the connection port 21 is hardly obstructed by secretion such as saliva, and the measurement can be prevented from being disturbed.

Figure 3:
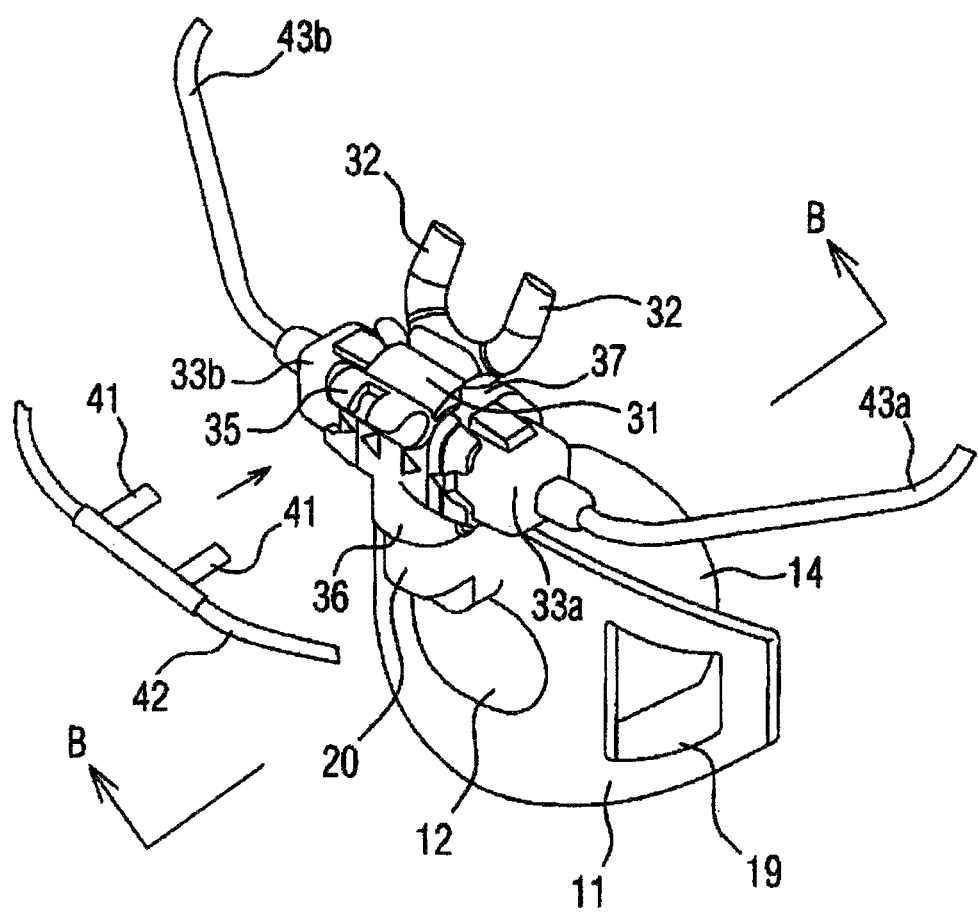
FIG. 3 is a perspective view of a bite block including a respiration information collecting adaptor of the embodiment of the invention.
Figure 4:
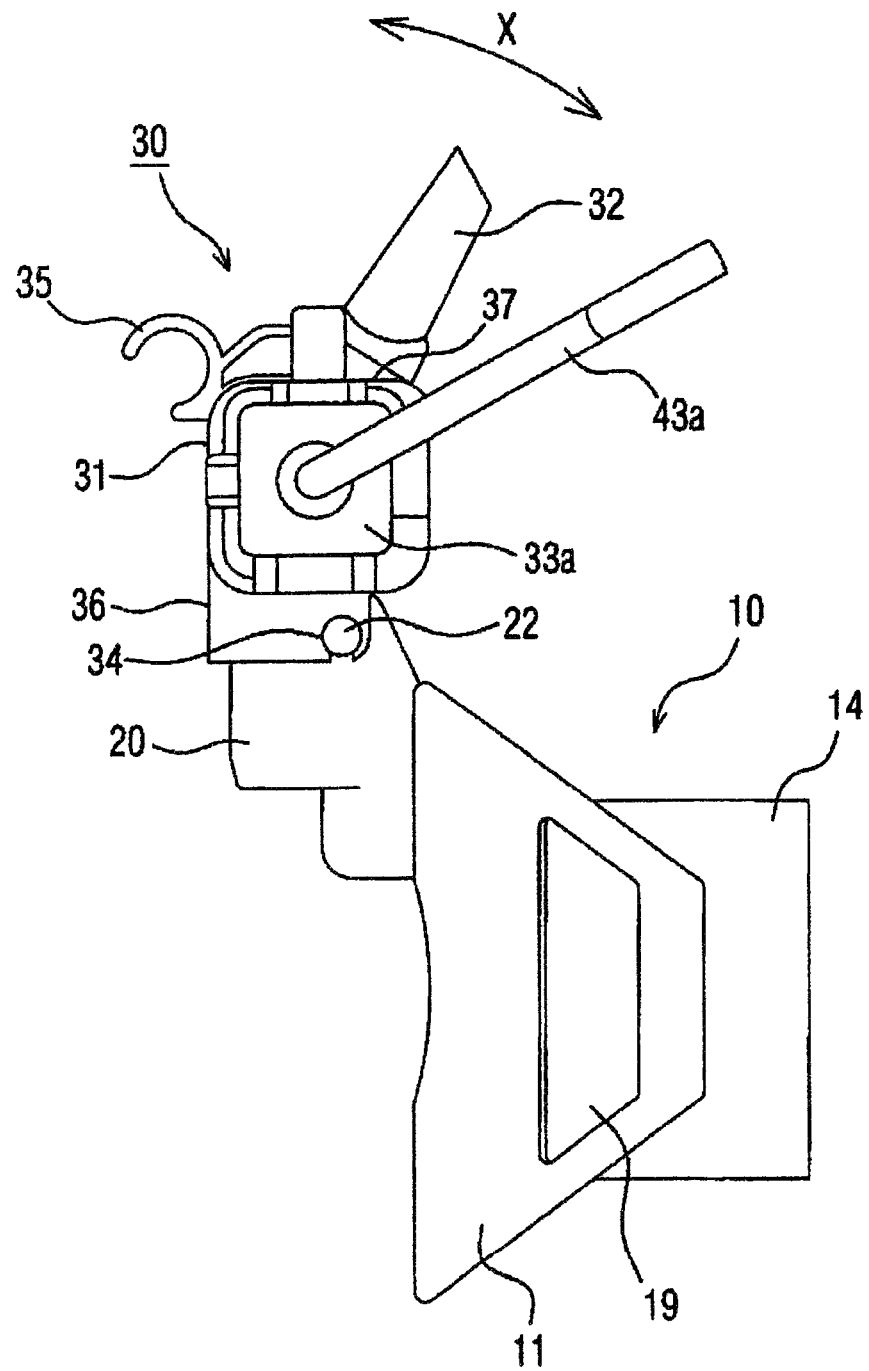
FIG. 4 is a side view of the bite block including the respiration information collecting adaptor of the embodiment of the invention.
Figure 5:
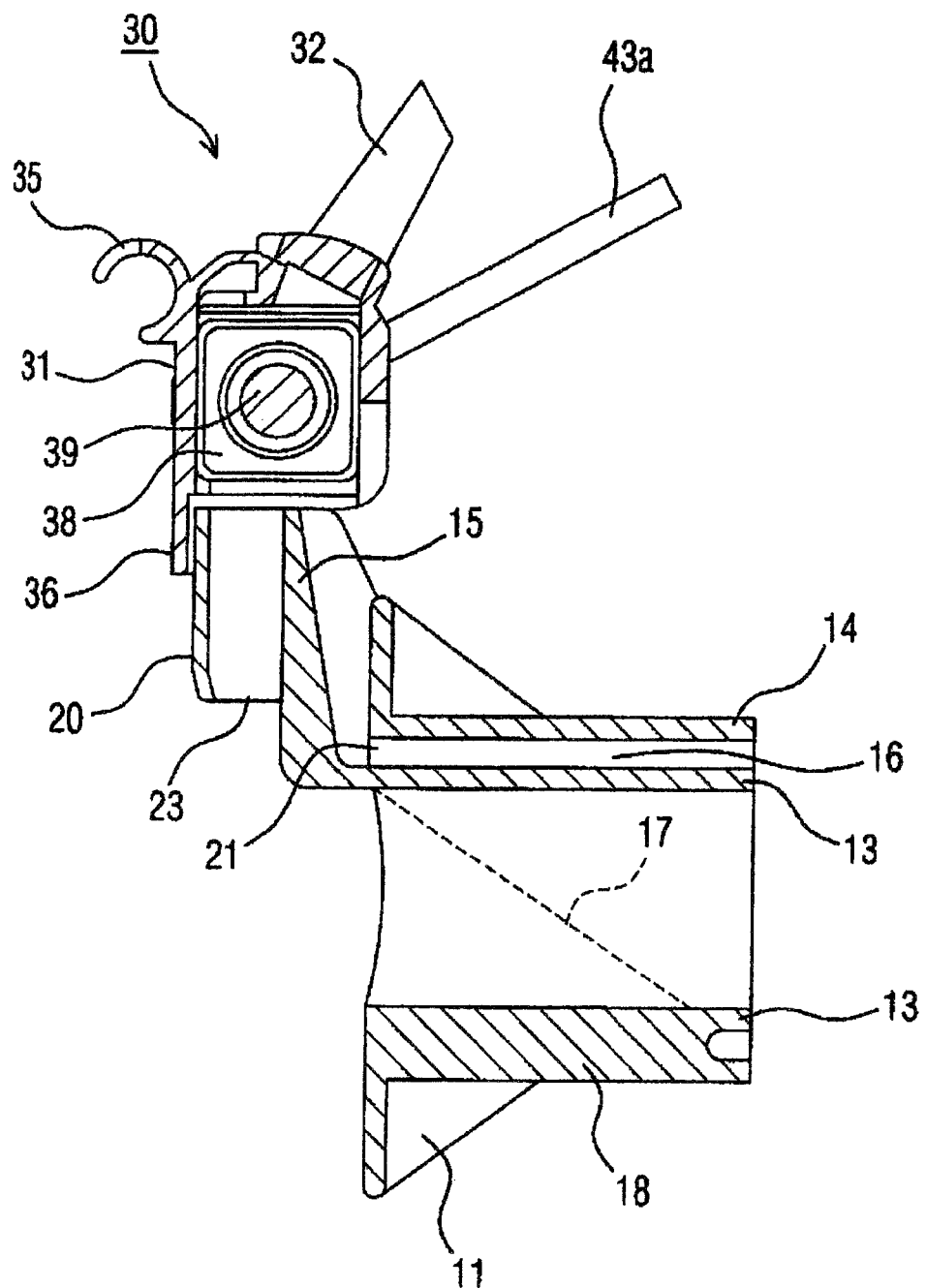
FIG. 5 is a sectional view taken along B-B in FIG. 3.
Figure 6:
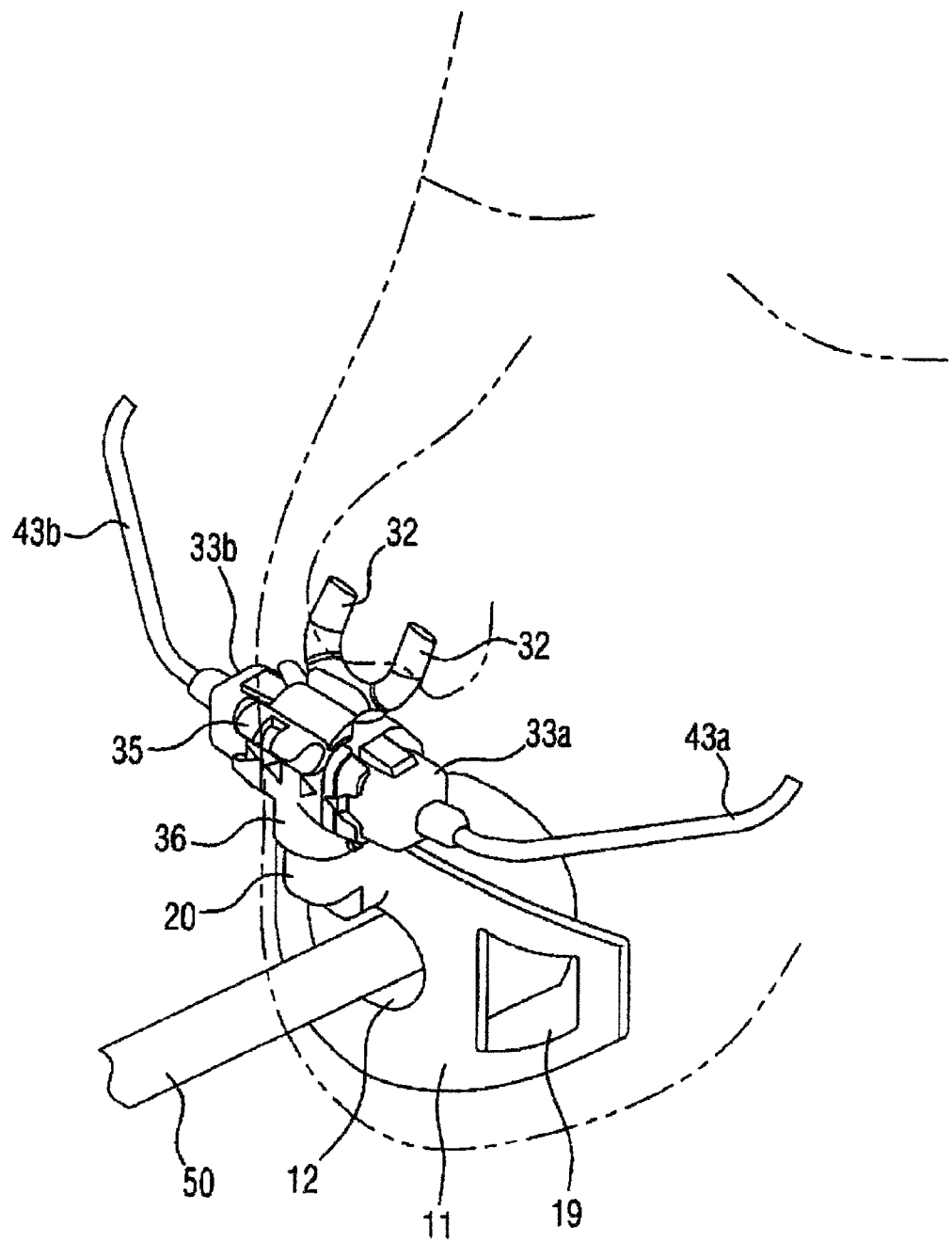
FIG. 6 is a perspective view showing a use state of the embodiment of the invention.

FIG. 3 is a perspective view of an embodiment in which the bite block 10 includes the respiration information collecting adaptor 30, FIG. 4 is a side view showing a respiration information collecting apparatus in which the embodiment is used, FIG. 5 is a sectional view, and FIG. 6 is a perspective view. In the respiration information collecting adaptor 30, a substantially cubic airway case 31 includes nasal tubes 32, and a carbon dioxide sensor 33 configured by a light emitting element 33a and a light receiving element 33b. The carbon dioxide sensor 33 is an example of a unit for collecting respiration information.

In the airway case 31, expiration from the nostrils is introduced into a chamber 38 of the airway case 31. The number of the nasal tubes 32 is two, and the nasal tubes are inserted into the nostrils, respectively. The two nasal tubes 32 are integrated with the airway case 31 in a basal portion 37.

The light emitting element 33a is coupled to one side portion of the airway case 31, and the light receiving element 33b is coupled to the other side portion. The light emitting surface of the light emitting element 33a, and a measurement window 39 which is the light receiving surface of the light receiving element 33b are opposed to each other across the chamber 38 of the airway case 31. Lead wires 43a, 43b are connected to the light emitting element 33a and the light receiving element 33b, respectively, and extend to a measuring apparatus.

The notched holes 34 are formed in the both sides of a lower portion of the airway case 31, respectively. The bosses 22 disposed on the bite block 10 are fitted to the holes, so that, as indicated by the arrow X in FIG. 4, the respiration information collecting adaptor 30 is swingable around the bosses 22, and the attitude of the respiration information collecting adaptor 30 is adjustable. A lower portion of the chamber 38 of the airway case 31 is opened and surrounded by a surrounding wall 36. When the bosses 22 are fitted to the notched holes 34, a state where the sample port 20 is covered by the surrounding wall 36 of the chamber 38 is produced.

A grip portion 35 having a tube-like shape in which a slightly large groove is formed in a side portion is formed at an upper position of the front face of the airway case 31 in the use state. The gripping portion 35 grips prongs 41 for supplying oxygen, by means of elasticity (FIG. 3). An oxygen supply tube 42 is connected to the prongs 41, so that oxygen is supplied from an oxygen supply source. The prongs 41 extend to the vicinities of and just below the nostrils through an upper face portion of the airway case 31 in the use state, so that the oxygen ejected from the tip ends of the prongs 41 can be sucked by the subject by means of nasal respiration. It is a matter of course that the position of the grip portion 35, the directions of the tip ends of the prongs 41, and the like are mere examples. As described above, the respiration information collecting adaptor 30 includes the grip portion 35 for, in a state where the bite block 10 is attached to the subject, causing the tip ends of the prongs 41 which supply oxygen, to be positioned near the nasal cavity or oral cavity of the subject, and holding the prongs 41.

In the thus configured embodiment, a band (not shown) attached to holes 19 which are opened in the both sides of the plate portion 11 makes one round around the face and the back of the head in FIG. 6 to support the bite block, and the measurement is performed in the following manner. A conduit pipe 50 of an endoscope is inserted through the hole 12 of the plate portion 11. A part of expiration due to mouth respiration of the subject reaches the sample port 20 through the gas flow path 16 formed between the first and second walls 13, 14 of the bite block 10, and the connection port 21. An opening which is formed in a lower portion of the chamber 38 of the airway case 31 is opposed to an upper portion of the sample port 20. The expiration reaches the chamber 38 of the airway case 31, and is then subjected to the measurement of the carbon dioxide sensor 33.

By contrast, expiration due to nasal respiration reaches the chamber 38 of the airway case 31 through the nasal tubes 32 to be subjected to the measurement of the carbon dioxide sensor 33, and then reaches the sample port 20 through the portion of the surrounding wall 36 of the lower portion of the chamber 38 to be discharged from the hole 23 through the chamber in front of the divider 15. The oxygen supply from the oxygen supply source is performed through the oxygen supply tube 42 by the prongs 41.

Figure 7:
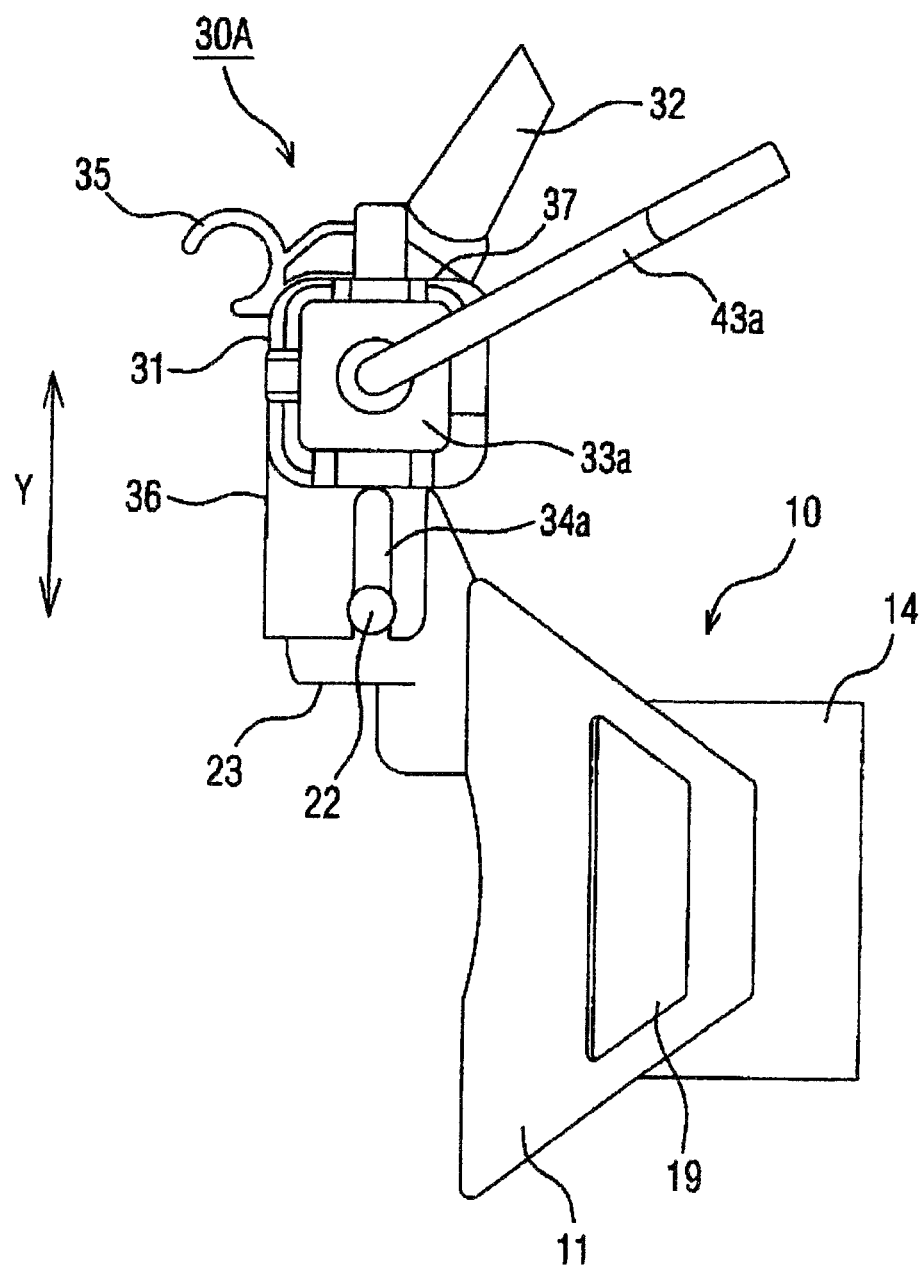
FIG. 7 is a side view of a bite block of a modification of the embodiment of the invention.

FIG. 7 is a side view of an embodiment of a bite block configured by using a respiration information collecting adaptor 30A of a modification. The respiration information collecting adaptor 30A includes notched oblong holes 34a which are formed in the both sides of a lower portion of the airway case 31, respectively. In a state where the notched oblong holes 34a are fitted to the bosses 22, the holes support the respiration information collecting adaptor 30A at arbitrary positions of the oblong holes. Therefore, the respiration information collecting adaptor 30A is movable in the vertical direction in the figure as shown by the arrow indicated by Y in the figure. In this way, the embodiment includes the adjusting mechanism which adjusts the distance from the sample port 20 to the respiration information collecting adaptor 30A. Of course, the adjusting mechanism serves also as an attitude adjusting mechanism which enables the rotation in the direction of arrow X shown in FIG. 4.

According to an aspect of the invention, the space which is configured by the bicylindrical structure of the first and the second walls functions as a flow path for a gas. As compared with a hole in the related art, the flow path can be widened, so that the flow path is hardly obstructed by secretion such as saliva. Therefore, the measurement can be prevented from being disturbed, and an accurate measured value can be obtained.

According to an aspect of the invention, the gas flow path includes the slope which is directed from the sample port toward the peripheral edges of the first and second walls. Therefore, the slope functions to make secretion such as saliva hardly flowable toward the sample port, whereby the measurement can be prevented from being disturbed, and an accurate measured value can be obtained. Furthermore, the bite block includes the adjustor coupled to the respiration information collecting adaptor and configured to adjust the attitude of the respiration information collecting adaptor and the distance between the sample port and the respiration information collecting adaptor. Therefore, the attitude of the respiration information collecting adaptor can be adjusted, and the distance between the sample port and the respiration information collecting adaptor can be adjusted.

According to an aspect of the invention, the sample port includes the divider that partitions the interior into the first chamber communicating with the flow path and the second chamber communicating with the outside. Therefore, expiration due to nasal respiration which reaches through the respiration information collecting adaptor attached to the attaching portion can reach the first chamber, and can be discharged from the second chamber through the first chamber.

What is claimed is:

1. A bite block comprising:
   a first wall defining a hole into which a conduit pipe is to be inserted;
   a second wall surrounding the first wall to define a flow path with the first wall; and
   a sample port communicating with the flow path, wherein
   the flow path includes a slope circumferentially formed between the first wall and the second wall and extending from the sample port while sloping downward toward peripheral edges of the first and second walls.

2. The bite block according to claim 1, further comprising:
   an attaching portion to which a respiration information collecting adaptor is to be attached.

3. The bite block according to claim 1, wherein
   the flow path includes a slope connected from the sample port to peripheral edges of the first and second walls.

4. The bite block according to claim 1, further comprising:
   an adjustor provided at the sample port and coupled to a respiration information collecting adaptor, the adjustor configured to adjust an attitude of the respiration information collecting adaptor and a distance between the sample port and the respiration information collecting adaptor.

5. The bite block according to claim 1, wherein
   the sample port includes a divider partitioning an interior into a first chamber communicating with the flow path and a second chamber communicating with an outside.

6. The bite block according to claim 1, further comprising:
   an attaching portion; and
   a respiration information collecting adaptor attached to the attaching portion and configured to collect respiration information.

7. The bite block according to claim 6, wherein
   the respiration information collecting adaptor includes a holder holding a prong which supplies oxygen, and
   when the bite block is attached to a subject, a tip end of the prong is positioned near a nasal cavity or oral cavity of the subject.

8. The bite block according to claim 1, wherein
   the first wall has a cylindrical shape,
   the conduit pipe is connected to an endoscope or a rigid scope,
   the flow path is defined by a space between the first wall and the second wall,
   and a gas in the oral cavity is directed to the sample port through the flow path.

9. The bite block according to claim 1, wherein
   an end of the first wall to be opposed to an oral cavity of a subject is in plane with an end of the second wall to be opposed to the oral cavity of the subject.

10. The bite block according to claim 1, wherein
    the hole defined by the first wall is to be communicated with an outside and an oral cavity of a subject,
    the flow path defined by the first wall and the second wall is to be communicated with the sample port and the oral cavity of the subject,
    and the hole and the flow path are separated with each other.

* * * * *